United States Patent
Kido et al.

(10) Patent No.: US 11,951,229 B2
(45) Date of Patent: Apr. 9, 2024

(54) LIQUID HEMOSTATIC MEDICAL MATERIAL

(71) Applicants: AOBAKASEI KABUSHIKI KAISHA, Sendai (JP); OSAKA CITY UNIVERSITY IN UNIVERSITY PUBLIC CORPORATION OSAKA, Osaka (JP)

(72) Inventors: Hirotsugu Kido, Sendai (JP); Katsunori Chiba, Sendai (JP); Hironori Arima, Osaka (JP); Kenji Ohata, Osaka (JP)

(73) Assignees: AOBAKASEI KABUSHIKI KAISHA, Miyagi (JP); OSAKA CITY UNIVERSITY IN UNIVERSITY PUBLIC CORPORATION OSAKA, Miyagi (JP)

( * ) Notice: Subject to any disclaimer, the term of this patent is extended or adjusted under 35 U.S.C. 154(b) by 167 days.

(21) Appl. No.: 17/407,982

(22) Filed: Aug. 20, 2021

(65) Prior Publication Data

US 2022/0054701 A1 Feb. 24, 2022

(30) Foreign Application Priority Data

Aug. 20, 2020 (JP) ................................. 2020-139696
Jun. 23, 2021 (JP) ................................. 2021-104461

(51) Int. Cl.
*A61L 26/00* (2006.01)
(52) U.S. Cl.
CPC ....... *A61L 26/0038* (2013.01); *A61L 26/0004* (2013.01); *A61L 26/0023* (2013.01); *A61L 26/0047* (2013.01); *A61L 2400/04* (2013.01)

(58) Field of Classification Search
None
See application file for complete search history.

(56) References Cited

U.S. PATENT DOCUMENTS 3,654,083 A * 4/1972 Moelker et al. ....... C12N 11/18
435/177
2011/0110882 A1 5/2011 Preiss-Bloom et al.

FOREIGN PATENT DOCUMENTS

EP 2 487 206 A2 8/2012
JP 2004-261222 A 9/2004
(Continued)

OTHER PUBLICATIONS

Wikipedia online "Dextrose Equivalent" (Year: 2023).*
(Continued)

*Primary Examiner* — Isis A Ghali
(74) *Attorney, Agent, or Firm* — Oliff PLC

(57) ABSTRACT

To provide a liquid medical material maintaining a colloid in a more sol form than a solid at normal temperature, having a higher function as a wound dressing material and a hemostatic material than fibrin glue, and being able to be produced safely and inexpensively. A gelatin aqueous solution including calcium at a concentration of 0.2 M or more and 1.0 M or less, and having a concentration of 5% by weight or more and 40% by weight or less, an average molecular weight of 80,000 or more and 120,000 or less, and a molecular weight distribution of 20,000 or more and 300,000 or less, and transglutaminase inducing crosslinking of the gelatin, are included. It is preferable that the calcium has a concentration of 0.2 M or more and 0.7 M or less, the gelatin has a bloom of 160 or more and 250 or less, and the transglutaminase has activity per unit of 36 U/ml to 400 U/ml.

5 Claims, 2 Drawing Sheets

(A) DE value (B) Average molecular weight

(56) References Cited

FOREIGN PATENT DOCUMENTS

| JP | 2011-525128 A | 9/2011 |
| JP | 2020-059653 A | 4/2020 |
| JP | 2020-130536 A | 8/2020 |
| JP | 2020-130541 A | 8/2020 |
| WO | 2008/076407 A2 | 6/2008 |
| WO | 2009/057802 A1 | 5/2009 |
| WO | 2010/041636 A1 | 4/2010 |

OTHER PUBLICATIONS

May 11, 2022 Office Action issued in Chinese Patent Application No. 202110960733.X.
Jan. 14, 2022 Extended Search Report issued in European Patent Application No. 21191221.7.
Aug. 12, 2022 Office Action issued in Chinese Patent Application No. 202110960733.X.

* cited by examiner

LIQUID HEMOSTATIC MEDICAL MATERIAL

FIELD OF THE INVENTION

This invention relates to a liquid medical material.

DESCRIPTION OF RELATED ART

Tissue occlusion to prevent leakage of a body fluid (blood, tissue fluids, and the like) caused by tissue damage of a living body is important clinically, for example, in surgery. Effectively suppressing leakage of a body fluid from a damage site can be life saving during surgery and improve the quality of life (QOL) after surgery in a patient.

Hemostasis is considered to be emphasized clinically. The reasons for this can include the followings.
1. Blood loss is one of the major causes of death. Causes of blood loss include serious traumatic injuries, aneurysm, esophageal and gastric ulcers, esophageal varix rupture, and the like. In particular, probability of death rises when hemostatic therapy cannot be done in the emergency.
2. Hemorrhage during surgery is a major concern. Hemorrhage causes systemic infectious diseases or organ dysfunction. Hemorrhage interrupts the surgical field. Furthermore, removal of the blood leads to a delay of surgery.
3. Hemorrhage is a problem also in carrying out minimally invasive surgery (for example, laparoscopic surgery). When hemorrhage cannot be sufficiently suppressed, the surgery may need to be changed to incision surgery.

Examples of the existing hemostasis methods include the followings.
1. Methods of directly compressing the blood vessel at the site of hemorrhage (astriction). Disadvantages of this hemostatic method include that the time and effort are required, pressure needs to be maintained, and further there is a possibility of hematoma formation in the patient.
2. Other hemostasis methods by physical means include methods of clamping or clipping near the site of hemorrhage, or methods of placing a plug or sponge on the site of hemorrhage. Disadvantages of these hemostasis methods include difficulty in handling when bleeding occurs from a large number of microvessels.
3. A method of clotting the blood by heat and cauterizing the bleeding vessel (electrocautery). Disadvantages of this method include that the surrounding tissue is subjected to thermal injury and a patient undergoes increased invasion, and that medical instruments are needed and expert skill is required (this method cannot be used outside of medical institutions).

Examples of existing hemostatic materials include:
1. Alginic acid
2. Gelatin sponges
3. Collagen fibers
4. Fibrin glue
5. Self-tissue synthetic peptide Of the above, collagen fibers and fibrin glue are often used clinically as effective hemostatic materials.

Blood vessel suture may be needed not only for cardiovascular surgery, but also for general intraperitoneal surgery. Since leakage of a small amount of blood occurs from a blood vessel suture site after surgery, a hemostatic material that continuously suppresses the leakage is required.

Bile fistula or pancreatic juice fistula is a symptom in which leakage of bile or pancreatic juice due to biliary tract system surgery or pancreatitis or pancreatic surgery adversely affects other organs. Currently, a substance capable of effectively suppressing the leakage of bile or pancreatic juice and clinically applicable is not known. Therefore, a method for safely and effectively preventing bile or pancreatic juice fistula is desired.

A disease state of air leakage in the lungs due to spontaneous pneumothorax is known in which the alveolar sac is ruptured or traumatic pneumothorax caused by rib fracture or catheter paracentesis. Depending on symptoms, there is no choice but to wait for natural healing. One of the simple and highly safe methods for treating pneumothorax is a method of simply providing an upper layer on the affected area and allowing it to adhere to the lung tissue and to occlude the cyst hole.

The development of endoscopic techniques has led to the development of techniques for endoscopically removing lesions. In particular, surgical methods have been established for endoscopic excision of lesions such as polyps or early-stage cancer (superficial cancer found to be without lymph node metastasis) in the gastrointestinal tract including the esophagus, stomach and intestines. In endoscopic mucosal resection, in general, hypertonic saline or the like is injected into the submucous layer including a lesion site to protrude the lesion site, and the tissue containing the lesion site is excised by electrocautery while the excision site is held.

In the technique, a solution such as hypertonic saline is injected into the submucosal layer in order to separate the lesion site from the muscularis propria, but there is a problem that the protuberance of the lesion site cannot be maintained during the surgery with a low viscosity solution such as saline, and an injection solution capable of maintaining the protuberance of the diseased site during the surgery has been desired.

The development of catheter therapy has led to establishment of surgical methods for killing tumors, myomas, and the like, by occluding arteries that flow into lesions such as tumors and myomas that are controlled by blood flow. Specifically, the methods include hepatic artery occlusion, uterine artery occlusion, and cerebral artery occlusion.

In this technique, fluids such as urethane precursors and ethylene vinyl alcohol are injected to occlude the artery, but they are definitely biotoxic, and therefore, the use thereof is limited unless they are serious. Thus, it is desired to develop infusion liquid that is not at risk of infection and has low toxicity.

Furthermore, an injection solution in which an anticancer agent or a contrast agent can be required.

Thus, in recent years, highly regulated self-organizing peptide has attracted attention because of their physical, chemical, and biological properties as a new material (see Patent Literature 1). The peptide has a property that a large number of peptide molecules are regularly arranged to form a self-association body by the amino acid sequence.

The self-organizing peptide has a structure in which electrically charged hydrophilic amino acids and electrically neutral hydrophobic amino acids alternate each other, and positive charge and negative charge are distributed alternately, and has a (3-structure in physiological pH and salt concentration.

In application of the self-organizing peptide for hemostasis, persistent leakage of the blood from the tip end of the liver incision site, and complete hemostasis has not been achieved. The reason for incomplete hemostasis is assumed to be because of insufficient adhesion between the self-organizing peptide gel and the tissue. Therefore, further improvements are needed to bring the hemostatic effect of the self-organizing peptide to clinically applicable levels.

A polyamine-aldehyde system, the gelatin which is clinically used like fibrin glue and is gelled by adding formaldehyde or glutaraldehyde as cross-linking agents, has a possibility of physical impediment such as vascular occlusion and a high degree of neurological and tissue disorder by low molecular weight aldehydes, and therefore, is far from satisfactory.

Many studies have been conducted in order to overcome these problems. For example, adhesives based on formation of a crosslinked Schiff base using dextran and ε-poly-L-lysine (hereinafter, also simply referred to as ε-PLL) including food additives as raw materials are being studied (see, for example, Patent Literature 2).

Furthermore, as an adhesive having high strength, a tissue adhesive including a derivative obtained by active-esterifying citric acid and protein such as collagen as an adhesive component has also been studied (see, for example, Patent Literature 3).

Furthermore, a composition that can be used as a wound dressing material and a hemostatic material, which contains cross-linkable gelatin, transglutaminase, calcium, and urea in a solution obtained by combining an acetic acid buffer solution and a citric acid buffer solution (see, for example, Patent Literature 4).

CITATION LIST

Patent Literature 1: WO2010/041636 A1
Patent Literature 2: WO2009/057802 A1
Patent Literature 3: JP-A-2004-261222
Patent Literature 4: JP-A-2011-525128

SUMMARY OF THE INVENTION

However, a tissue occlusion agent described in Patent Literature 1 is a self-organizing peptide, but has a problem that the hemostatic force is lower than that of fibrin glue.

Furthermore, the adhesive including the ε-PLL raw material described in Patent Literature 2 has a gel strength inferior to that of fibrin glue as a commercially available hemostatic material, and has a problem that the adhesive has insufficient strength as a hemostatic material.

In the tissue adhesive described in Patent Literature 3, since the active ester compound is chemically unstable and cannot be stored in an aqueous solution for a long period of time, it is necessary to dissolve the tissue adhesive in a solvent immediately before use, and the solvent has a risk of adversely affecting a living body. Moreover, it has a problem that it is highly likely to cause difficulty since it is unable to use the tissue adhesive immediately when a doctor urgently uses it during a surgery and so on, for example.

Furthermore, these adhesives have the problem of being very expensive.

The composition using gelatin and transglutaminase disclosed in Patent Literature 4 requires urea to stabilize the gel, so that the production process is complicated and has a problem in safety.

The present invention has been made focusing on such problems, and has an object to provide a liquid medical material maintaining a colloid in a more sol form than a solid at normal temperature, having a higher function as a wound dressing material and a hemostatic material than fibrin glue, and being able to be produced safely and inexpensively.

The present inventors have extensively studied to achieve the above-mentioned object, resulting in finding that there are optimum types of gelatin, concentration of gelatin, and calcium concentration, and have completed the present invention.

In other words, a liquid medical material in accordance with the present invention includes a gelatin aqueous solution including calcium at a concentration of 0.2 M or more and 1.0 M or less, and having a concentration of 5% by weight or more and 40% by weight or less, an average molecular weight of 80,000 or more and 120,000 or less, and a molecular weight distribution of 20,000 or more and 300,000 or less; and transglutaminase inducing crosslinking of the gelatin.

It is preferable in the liquid medical material in accordance with the present invention that the calcium has a concentration of 0.2 M or more and 0.7 M or less, the gelatin has a bloom of 160 or more and 250 or less, the transglutaminase has activity per unit of 36 U/ml to 400 U/ml.

It is preferable in the liquid medical material in accordance with the present invention that a rate of a calcium concentration [M] with respect to a gelatin weight concentration [wt %] in the gelatin aqueous solution is 0.005 M/wt % to 0.040 M/wt %.

It is preferable that the liquid medical material in accordance with the present invention includes dextran having a DE value of 10 or more and 25 or less, and an average molecular weight of 5000 or more and 25000 or less, in addition to the transglutaminase.

It is preferable that the liquid medical material in accordance with the present invention includes dextran having a DE value of 25 or more, and an average molecular weight of 5000 or less, in addition to the transglutaminase.

It is preferable that the liquid medical material in accordance with the present invention includes, for example, a tissue adhesive for living organisms, a hemostatic material, a cell preservation solution, an organ preservation solution, an artificial ointment, an alveolar bone reconstruction agent, an anti-adhesion agent for biological tissues, a mucosal protuberance agent, an anti-post-bleeding agent, a wound dressing material, an implant auxiliary material, or an embolization material in endovascular therapy.

In particular, it is preferable that the liquid medical material in accordance with the present invention is a venous hemostatic material.

The liquid medical material in accordance with the present invention maintains a colloid in a more sol form than a solid at normal temperature, has a higher function as a wound dressing material and a hemostatic material than fibrin glue, and can be produced safely and inexpensively.

The present invention can provide a liquid medical material maintaining a colloid in a more sol form than a solid at normal temperature, having a higher function as a wound dressing material and a hemostatic material than fibrin glue, and being able to be produced safely and inexpensively.

DETAILED DESCRIPTION OF THE INVENTION

Figure 1:
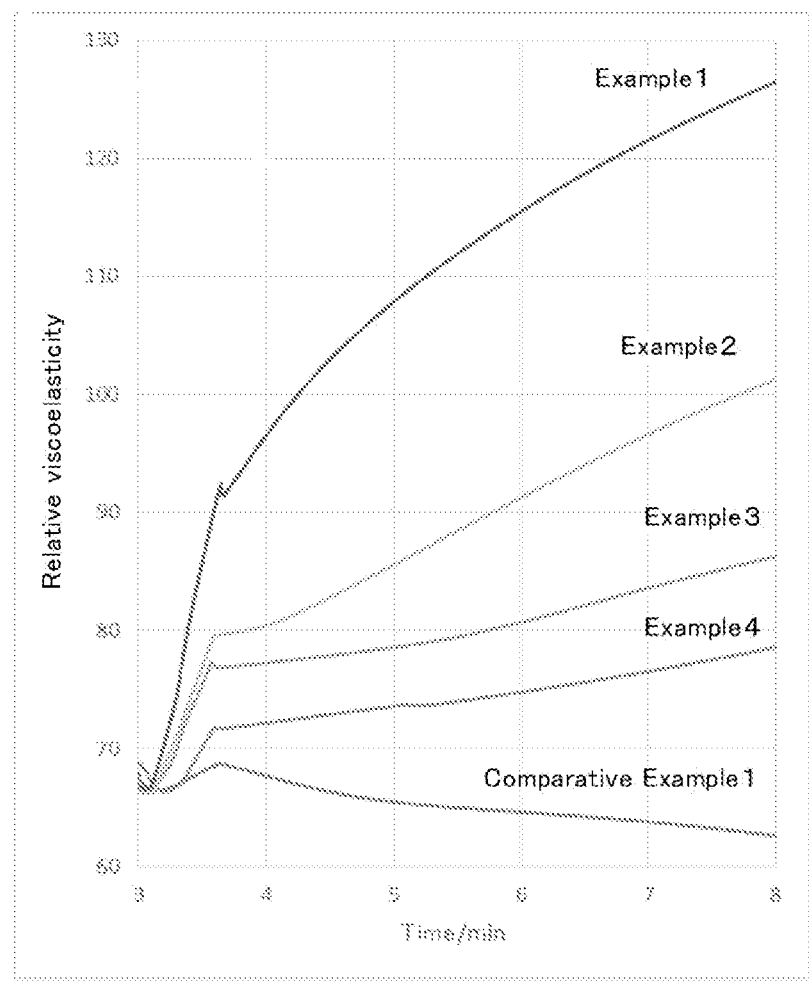
FIG. 1 is a graph showing a change of viscoelasticity of each of hemostatic materials when samples having different transglutaminase activity in Examples of the present invention.

Hereinafter, a liquid medical material of an embodiment of the present invention will be described.

A liquid medical material in accordance with the embodiment of the present invention includes a gelatin aqueous solution including calcium at a concentration of 0.2 M or more and 1.0 M or less, and having a concentration of 5% by weight or more and 40% by weight or less, an average molecular weight of 80,000 or more and 120,000 or less, and a molecular weight distribution of 20,000 or more and 300,000 or less; and transglutaminase inducing crosslinking of the gelatin.

It is preferable that the calcium has a concentration of 0.2 M or more and 0.7 M or less, the gelatin has a bloom of 160 or more and 250 or less, the transglutaminase has activity per unit of 36 U/ml to 400 U/ml.

The calcium preferably includes, for example, calcium chloride, and calcium carbonate, and particularly preferably calcium chloride.

It is preferable that a rate of a calcium concentration [M] with respect to a gelatin weight concentration [wt %] in the gelatin aqueous solution is 0.005 M/wt % to 0.040 M/wt %.

It is preferable that dextran having a DE value of 10 or more and 25 or less, and an average molecular weight of 5000 or more and 25000 or less is included in addition to the transglutaminase.

Furthermore, it is preferable that dextran having a DE value of 25 or more, and an average molecular weight of 5000 or less is included in addition to the transglutaminase.

It is that the liquid medical material in accordance with the embodiment of present invention includes, for example, a tissue adhesive for living organisms, a hemostatic material, a cell preservation solution, an organ preservation solution, an artificial ointment, an alveolar bone reconstruction agent, an anti-adhesion agent for biological tissues, a mucosal protuberance agent, an anti-post-bleeding agent, a wound dressing material, an implant auxiliary material, or an embolization material in endovascular therapy.

In particular, it is preferable that the liquid medical material in accordance with the embodiment of present invention is a venous hemostatic material.

In the present invention, the "blood" may be human blood, or non-human blood.

The liquid medical material in accordance with the embodiment of the present invention maintains a colloid in a more sol form than a solid at normal temperature, has a higher function as a wound dressing material and a hemostatic material than fibrin glue, and can be produced safely and inexpensively.

In the liquid medical material of the embodiment of the present invention, a gelatin material is not solidified (gelled) under a condition at 25° C. and around 37° C. in the living organism, and then can be solidified in 300 seconds, preferably 90 seconds, and further preferably 30 seconds when transglutaminase is added.

In particular, when the liquid medical material is used in blood, solidification occurs at the same or faster rate than in the absence of blood, and a membrane having very high viscoelasticity can be formed.

When the liquid medical material is used for covering wound, when transglutaminase is mixed, solidification occurs very fast, and a membrane having very high viscoelasticity can be formed.

Example

Hereinafter, the present invention will be described with reference to Examples, but the present invention is not limited thereto. Note here that in the following Examples, "%" means "% by weight."

(Test 1)

The following gelatin/calcium aqueous solutions were prepared.

Types of Gelatin:

A: Acid-treated gelatin having an average molecular weight of 100,000 (distribution of 20,000 to 300,000)

B: Alkali-treated gelatin having an average molecular weight of 100,000 (distribution of 20,000 to 300,000)

C: Gelatin having an average molecular weight of 20,000 (polypeptide)

D: Gelatin having a molecular weight of approximately 100,000 (distribution of 80,000 to 120,000)

Concentration of gelatin: 5 to 40 wt % (5, 10, 20, 30, and 40 wt %)

Calcium concentration: 0.0 to 1.0 M (0, 0.2, 0.4, 0.5, 0.7, and 1.0 M)

(1) Gelatin aqueous solutions of A, B, C, and D, having concentrations of 5, 10, 20, 30, and 40 wt %, were prepared, respectively. Under a condition at 25° C., the gelatin aqueous solutions of A, B, and D were solidified at concentration of 5%. The gelatin aqueous solution of C was not solidified even at 40% and was in a flow state.

(2) Gelatin/calcium aqueous solutions of A, B, and D, having concentrations of gelatin and concentrations of calcium shown in Table 1 were prepared.

Under a condition at 25° C., a state of each of the gelatin/calcium aqueous solutions was observed, and evaluated for solidification, flow, or high viscosity.

Solidified: A state in which an aqueous solution does not move at all even if a sample is brought down.

Flow: A state in which an aqueous solution starts to move when a sample is brought down.

High viscosity: A state in which an aqueous solution starts to move gradually a few times after a sample is brought down.

TABLE 1

| A | | 0 | 0.2 | 0.4 | 0.5 | 0.7 | 1 |
|---|---|---|---|---|---|---|---|
| | | Calcium concentration [M] | | | | | |
| Gelatin concentration [wt %] | 5 | Solidified | Flow | Flow | Flow | Flow | Flow |
| | 10 | Solidified | Flow | Flow | Flow | Flow | Flow |
| | 20 | Solidified | High viscosity | Flow | Flow | Flow | Flow |
| | 30 | Solidified | Solidified | High viscosity | High viscosity | Flow | Flow |
| | 40 | Solidified | Solidified | Solidified | High viscosity | High viscosity | High viscosity |

| B | | 0 | 0.2 | 0.4 | 0.5 | 0.7 | 1 |
|---|---|---|---|---|---|---|---|
| | | Calcium concentration [M] | | | | | |
| Gelatin concentration [wt %] | 5 | Solidified | Flow | Flow | Flow | Flow | Flow |
| | 10 | Solidified | Flow | Flow | Flow | Flow | Flow |
| | 20 | Solidified | High viscosity | Flow | Flow | Flow | Flow |
| | 30 | Solidified | Solidified | High viscosity | High viscosity | Flow | Flow |
| | 35 | Solidified | Solidified | Solidified | High viscosity | High viscosity | Flow |
| | 40 | Solidified | Solidified | Solidified | High viscosity | High viscosity | High viscosity |

| D | | 0 | 0.2 | 0.4 | 0.5 | 0.7 | 1 |
|---|---|---|---|---|---|---|---|
| | | Calcium concentration [M] | | | | | |
| Gelatin concentration [wt %] | 5 | Solidified | Flow | Flow | Flow | Flow | Flow |
| | 10 | Solidified | Flow | Flow | Flow | Flow | Flow |
| | 20 | Solidified | Solidified | Flow | Flow | Flow | Flow |
| | 30 | Solidified | Solidified | Solidified | Solidified | Flow | Flow |
| | 40 | Solidified | Solidified | Solidified | Solidified | Solidified | Solidified |

From the above results, aqueous solutions that are not solidified, that is, aqueous solutions in a state having a high viscosity or in a flow state, at 25° C., are selected. The conditions for selection are as follows.

<Conditions>

A, B: 0%<suitable condition≤40% gelatin<concentration at which a gelatin aqueous solution is prepared 0.2 M calcium≤suitable condition≤1.0 M calcium<concentration at which a calcium aqueous solution is prepared C: 0%<suitable condition≤40% gelatin<concentration at which a gelatin aqueous solution is prepared, 0 M calcium≤suitable condition<concentration at which a calcium aqueous solution is prepared D: 0%<suitable condition<40% gelatin 0.2 M calcium≤suitable condition≤1.0 M calcium<concentration at which a calcium aqueous solution is prepared (Test 2)

In order to examine a range of suitable activity of transglutaminase, change of viscoelasticity of hemostatic materials using samples having different transglutaminase activity were measured.

Evaluation of samples having different transglutaminase activity was carried out using 20% gelatin containing 0.5 M CaCl$_2$) (bloom: 250, average molecular weight: 100,000). Table 2 shows transglutaminase activity of each sample. FIG. 1 shows measurement results of change of viscoelasticity.

TABLE 2

| Examples | Transglutaminase activity (as BSA) [U/ml] |
|---|---|
| Example 1 | 51.6 |
| Example 2 | 43.0 |
| Example 3 | 34.4 |
| Example 4 | 25.8 |
| Comparative Example 1 | 17.2 |

The results of FIG. 1 show that transglutaminase used for a crosslinking agent of the hemostatic material is preferably transglutaminase having transglutaminase activity [U/ml] of higher than 17.2, and more preferably higher than 34.4.

(Test 3)

A crosslinking evaluation test of a hemostatic material was carried out using a blood viscoelasticity testing device (product name "Sonoclot" manufactured by Sienco, Inc.). After the addition of transglutaminase, the relative viscoelasticity is increased by crosslinking. The inclination of the increase is defined as K, and is compared.

<Basic Experiment>

An experiment was carried out using calcium-containing gelatin shown in Table 3 and transglutaminase having relative activity of 51.6 U/ml. The results are shown in right column of Table 3.

TABLE 3

| | Composition | Inclination ( =K) (relative viscoelasticity/ time [/min] |
|---|---|---|
| Example 1 | 20% (bloom: 250, average molecular weight: 100,000) gelatin, 0.5M CaCl$_2$ | 45.9 |
| Example 2 | 30% (bloom: 250, average molecular weight: 100,000) gelatin, 0.7M CaCl$_2$ | 45.7 |
| Example 3 | 20% (bloom: 200, average molecular weight: 100,000) gelatin, 0.5M CaCl$_2$ | 32.4 |
| Comparative Example 1 | 25% (bloom: 300) gelatin, 2M CaCl$_2$ (prepared according to the existing patent) | 10.4 |

From the results, it is shown that in Comparative Example 1 prepared according to the existing patent, elongation of the initial viscoelasticity is poor, and solidification does not sufficiently occur over time, and that in Examples 1 to 3, elongation of the initial viscoelasticity is good and solidification easily occurs.

The 20% gelatin/0.2 M calcium aqueous solution (material a) of B of Test 1 was selected, and the crosslinking test by transglutaminase was carried out. The activity and concentration of transglutaminase (TG) used are shown in Table 4.

TABLE 4

| Name | Activity [U/g] | Concentration [mg/ml] | Product name |
|---|---|---|---|
| TGA | 86 | 6.0 | KS-CT (manufactured by Ajinomoto Co., Inc.) |
| TGB | 86 | 2.0 | KS-CT (manufactured by Ajinomoto Co., Inc.) |
| TGC | 86 | 0.6 | KS-CT (manufactured by Ajinomoto Co., Inc.) |

To 100 μL of the material a, 50 μL each of TG having concentrations was added, and the obtained product was stirred, and solidification time was measured. The results are shown in Table 5.

From the results of Table 5, TGA was selected as TG.

TABLE 5

| Name | Concentration [mg/ml] | Solidification time [min] |
|---|---|---|
| TGA | 6.0 | 3 |
| TGB | 2.0 | 6 |
| TGC | 0.6 | 15 |

A crosslinking test was carried out using transglutaminase and various gelatin/calcium aqueous solutions. Conditions of the samples subjected to the test are shown in Tables 6 and 7.

Furthermore, for comparison, Reference Examples were prepared as follows based on Patent Literature 4, and similarly, the cross-linking test was carried out.

Reference Example 1: A solution was prepared by mixing a 25% (w/w) gelatin solution including 2 M urea, 1 M calcium, and 0.1 M sodium acetate (the gelatin is pig acid-treated gelatin and has a bloom of 270) with 7.5% (w/w) microbial transglutaminase (10% w/w mTG-ACTIVA-TG manufactured by Ajinomoto Co., Inc.) solution including 0.5 M sodium acetate and calcium-independent microbial transglutaminase (mTG).

Reference Example 2: A solution was prepared using 0.5M sodium citrate instead of 0.5 M sodium acetate in Reference Example 1.

TABLE 6

| Sample No. | B-system [%] | Calcium concentration [M] | Solidification time [sec] | Surgical field | Examples |
|---|---|---|---|---|---|
| 1 | 5 | 0.2 | 90 | Open | Example |
| 2 | | 0.4 | 420 | | Co. Example |
| 3 | | 0.5 | 450 | | Co. Example |
| 4 | | 0.7 | 460 | | Co. Example |
| 5 | 10 | 0.2 | *) | | Co. Example |
| 6 | | 0.4 | 80 | Open | Example |
| 7 | | 0.5 | 200 | Catheter | Example |
| 8 | | 0.7 | 350 | | Co. Example |
| 9 | 20 | 0.3 | 30 | Open | Example |
| 10 | | 0.4 | 25 | Open | Example |
| 11 | | 0.5 | 60 | Open | Example |
| 12 | | 0.7 | 350 | | Co. Example |
| 13 | 30 | 0.2 | N.D | | Co. Example |
| 14 | | 0.4 | 40 | Open | Example |
| 15 | | 0.5 | 50 | Open | Example |
| 16 | | 0.7 | 200 | Catheter | Example |
| 17 | 35 | 0.2 | N.D | | Co. Example |
| 18 | | 0.4 | N.D | | Co. Example |
| 19 | | 0.5 | 50 | Open | Example |
| 20 | | 0.7 | 140 | Catheter | Example |
| Re. Example 1 | | | 150 | | Co. Example |
| Re. Example 2 | | | 210 | | Co. Example |

*): A flow state became heterogeneous immediately after transglutaminase was added.
N.D.: A state is solid and cannot be mixed.

TABLE 7

| Sample No. | 20% gelatin | Bloom | Calcium concentration [M] | Solidification time [sec] | Surgical field | Examples |
|---|---|---|---|---|---|---|
| 21 | A-system | 200 | 0.2 | 40 | Open | Example |
| 22 | | | 0.4 | 30 | Open | Example |
| 23 | | | 0.5 | 100 | Catheter | Example |
| 24 | | | 0.7 | 350 | | Co. Example |
| 25 | B-system | 160 | 0.2 | 75 | Open | Example |
| 26 | | | 0.4 | 65 | Open | Example |
| 27 | | | 0.5 | 100 | Catheter | Example |
| 28 | | | 0.7 | 420 | | Co. Example |

TABLE 7-continued

| Sample No. | 20% gelatin | Bloom | Calcium concentration [M] | Solidification time [sec] | Surgical field | Examples |
|---|---|---|---|---|---|---|
| 29 | | 200 | 0.2 | 55 | Open | Example |
| 30 | | | 0.4 | 25 | Open | Example |
| 31 | | | 0.5 | 40 | Open | Example |
| 32 | | | 0.7 | 350 | | Co. Example |
| 33 | | 250 | 0.2 | 45 | Open | Example |
| 34 | | | 0.4 | 15 | Open | Example |
| 35 | | | 0.5 | 85 | Open | Example |
| 36 | | | 0.7 | 250 | Catheter | Example |
| 37 | D-system | 200 | 0.2 | *) | | Co. Example |
| 38 | | | 0.4 | *) | | Co. Example |
| 39 | | | 0.5 | *) | | Co. Example |
| 40 | | | 0.7 | 150 | Catheter | Example |

*): A flow state became heterogeneous immediately after transglutaminase was added.

A liquid medical material preferably has functions that under a condition at 25° C., the liquid medical material is not solidified before crosslinking, does not form a heterogeneous lump even when mixed, and has solidification time after crosslinking (the time at which a viscosity becomes the square or more of its original state (for example, 10 cps→100 cps) of 300 seconds or less, more preferably 90 seconds or less, and particularly 30 seconds or less.

It is considered to be difficult to use materials that are not solidified under a condition at 25° C. and not solidified in 85 seconds in an open surgical field. Furthermore, it is considered to be difficult to use materials that are not solidified in 300 seconds in a catheter surgical field.

When 100 μL of blood, 100 μL of 20% gelatin/0.2 M calcium aqueous solution of B (material a), and 50 μL of transglutaminase are mixed, a solidification time was measured. Conditions of samples subjected to the test are shown in Table 8.

As shown in Table 8, it is considered to be difficult to use a material, which is not solidified under a condition at 25° C. and not solidified in 60 seconds, for hemostasis, in particular, arterial hemostasis in an open surgical field. Furthermore, it is considered to be difficult to use a material that is not solidified for 200 seconds for hemostasis in a catheter surgical field.

(Test 4)

The following gelatin/calcium aqueous solution was prepared. An alkali-treated gelatin (concentration of gelatin: 20 wt %)/0.5 M calcium aqueous solution having an average molecular weight of 100,000 (distribution: 20,000 to 300,000). A cross-linking test using transglutaminase was carried out using this gelatin aqueous solution.

As transglutaminase (TG), transglutaminase (Name: TGA, product name: KS-OT (manufactured by Ajinomoto, Inc.)) having activity of 86 U/g, concentration of 6 mg/ml, and polysaccharide concentration of 600 mg/ml was used.

TABLE 8

| Sample No. | 20% gelatin | Bloom | Calcium concentration [M] | Solidification time [sec] | Surgical field | Examples |
|---|---|---|---|---|---|---|
| 41 | A-system | 200 | 0.2 | N.D. | | Co. Example |
| 42 | | | 0.4 | 24 | Open | Example |
| 43 | | | 0.5 | 80 | Catheter | Example |
| 44 | | | 0.7 | 280 | Catheter | Example |
| 45 | B-system | 160 | 0.2 | N.D. | | Co. Example |
| 46 | | | 0.4 | 52 | Open | Example |
| 47 | | | 0.5 | 95 | Catheter | Example |
| 48 | | | 0.7 | 360 | | Co. Example |
| 49 | | 200 | 0.2 | N.D. | | Co. Example |
| 50 | | | 0.4 | 22 | Open | Example |
| 51 | | | 0.5 | 33 | Open | Example |
| 52 | | | 0.7 | 280 | Catheter | Example |
| 53 | | 250 | 0.2 | N.D. | | Co. Example |
| 54 | | | 0.4 | 12 | Open | Example |
| 55 | | | 0.5 | 15 | Open | Example |
| 56 | | | 0.7 | 220 | Catheter | Example |
| 57 | D-system | 200 | 0.2 | N.D. | | Co. Example |
| 58 | | | 0.4 | N.D. | | Co. Example |
| 59 | | | 0.5 | N.D. | | Co. Example |
| 60 | | | 0.7 | 120 | Catheter | Example |

N.D.: When blood and transglutaminase were mixed with material a at 25° C., a state became heterogeneous.

Included polysaccharide was removed, and then the following five types of dextran were added at 600 mg/ml, respectively. Results of the cross-linking test were shown in right part, respectively.

Figure 2:
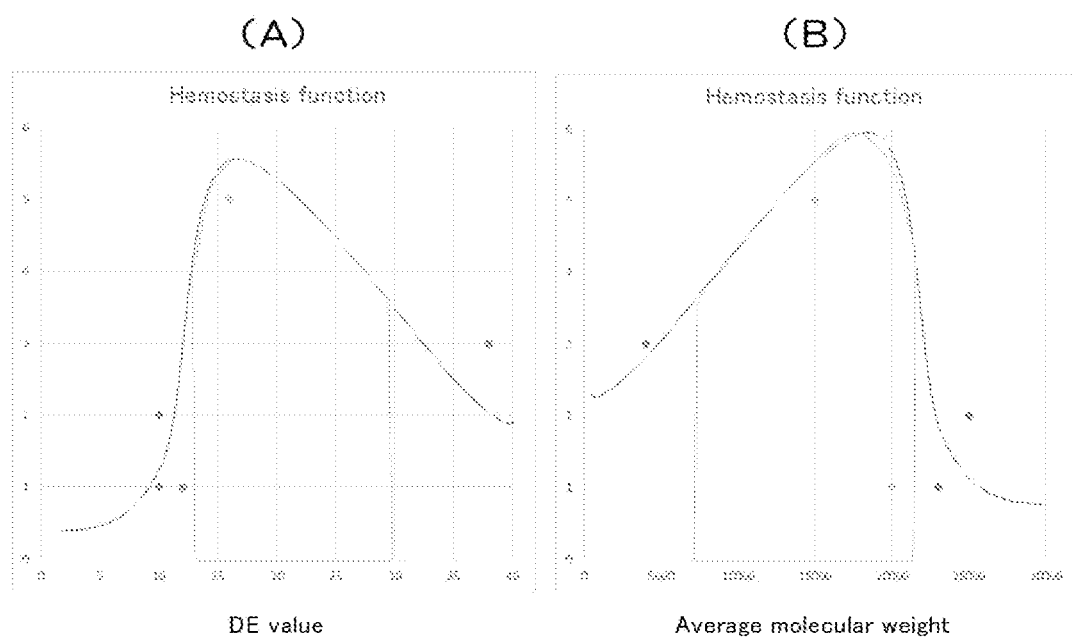
FIG. 2 includes (A) a graph illustrating a relation between a DE value and a hemostasis function and (B) a graph illustrating a relation between an average molecular weight and a hemostasis function, when dextran is included in addition to transglutaminase in Examples of the present invention.

(1) Dextran having a DE value of 38, an average molecular weight of 4000, and being porous: cross-linking reaction occurred within 5 minutes
(2) Dextran having a DE value of 16, an average molecular weight of 15000, and being porous: cross-linking reaction occurred within 30 seconds
(3) Dextran having a DE value of 10, an average molecular weight of 25000, and being porous: cross-linking reaction occurred
(4) Dextran having a DE value of 10, an average molecular weight of 23000, and not being porous: cross-linking test did not occur
(5) Dextran having a DE value of 12, an average molecular weight of 20000, and not being porous: cross-linking test did not occur Furthermore, for the hemostasis function, a case where the cross-linking test was not carried out is evaluated as 1, a case where the cross-linking reaction occurred is evaluated as 2, a case where the cross-linking reaction occurred within 5 minutes is evaluated as 3, a case where the cross-linking reaction occurred within 2 minutes is evaluated as 4, and a case where the cross-linking reaction occurred within 30 seconds is evaluated as 5. The relation between the DE value and the hemostasis function is shown in FIG. 2(A), and the relation between the average molecular weight and the hemostasis function is shown in FIG. 2(B).

From the above results, from the viewpoint of the hemostasis function, it is shown to be preferable that dextran having a DE value of 10 or more and 25 or less, and an average molecular weight of more than 5000 and 25000 or less is included in addition to transglutaminase. Furthermore, it is shown to be preferable that dextran having a DE value of 25 or more and an average molecular weight of 5000 or less is included in addition to transglutaminase.

What is claimed is:

1. A liquid medical material comprising:
   a gelatin aqueous solution including calcium at a concentration of 0.2 M or more and 1.0 M or less, and gelatin having a concentration of 5% by weight or more and 40% by weight or less, an average molecular weight of 80,000 or more and 120,000 or less, and a molecular weight distribution of 20,000 or more and 300,000 or less;
   transglutaminase configured to induce crosslinking of the gelatin; and
   porous dextran having a DE value of 10 or more and 25 or less, and an average molecular weight of 5000 or more and 25000 or less,
   wherein the calcium includes a compound selected from the group consisting of calcium chloride and calcium carbonate wherein the liquid material is hemostatic material.

2. The liquid medical material according to claim 1, wherein the calcium has a concentration of 0.2 M or more and 0.7 M or less, the gelatin has a bloom of 160 or more and 250 or less, the transglutaminase has activity per unit of 36 U/ml to 400 U/ml.

3. The liquid medical material according to claim 1, wherein a rate of a calcium concentration [M] with respect to a gelatin weight concentration [wt %] in the gelatin aqueous solution is 0.005 M/wt % to 0.040 M/wt %.

4. The liquid medical material according to claim 1, wherein the hemostatic material is a venous hemostatic material.

5. The liquid medical material according to claim 1, wherein the dextran has a DE value of 16 or more and 25 or less.

* * * * *